(12) United States Patent
Gupta

(10) Patent No.: US 7,527,784 B2
(45) Date of Patent: May 5, 2009

(54) WATER WASHABLE HAIR REMOVAL (DEPILATORY) COMPOSITIONS

(75) Inventor: Shyam K Gupta, Scottsdale, AZ (US)

(73) Assignee: Bioderm Research, Scottsdale, AZ (US)

( * ) Notice: Subject to any disclaimer, the term of this patent is extended or adjusted under 35 U.S.C. 154(b) by 710 days.

(21) Appl. No.: 11/162,209

(22) Filed: Aug. 31, 2005

(65) Prior Publication Data

US 2007/0048242 A1 Mar. 1, 2007

(51) Int. Cl.
*A61K 8/73* (2006.01)
(52) U.S. Cl. .................. 424/73; 424/70.13
(58) Field of Classification Search ............ None
See application file for complete search history.

(56) References Cited

U.S. PATENT DOCUMENTS 5,698,178 A * 12/1997 Goldenberg ........... 424/1.49

2003/0235539 A1* 12/2003 Mongiat et al. ........... 424/59
2005/0255134 A1* 11/2005 Hasenzahl et al. ........ 424/401

FOREIGN PATENT DOCUMENTS

WO WO02/085322 * 10/2002

* cited by examiner

*Primary Examiner*—Kamal A Saeed
*Assistant Examiner*—Valerie Rodriguez-Garcia

(57) ABSTRACT

Cosmetic hair removal (depilatory) compositions that provide complete hair removal in a single step and easy clean-up with water are disclosed. These viscous compositions are made of a mixture of a water soluble hair binding agent, a water soluble cross-linking agent for the hair binding agent, and a water soluble crystallization inhibitor agent, whereby the cross-linking of the hair binding agent by the cross-linking agent results in water washable hair binding compositions that do not crystallize during their use or storage.

17 Claims, 1 Drawing Sheet

Chemical Structure of Phytic Acid

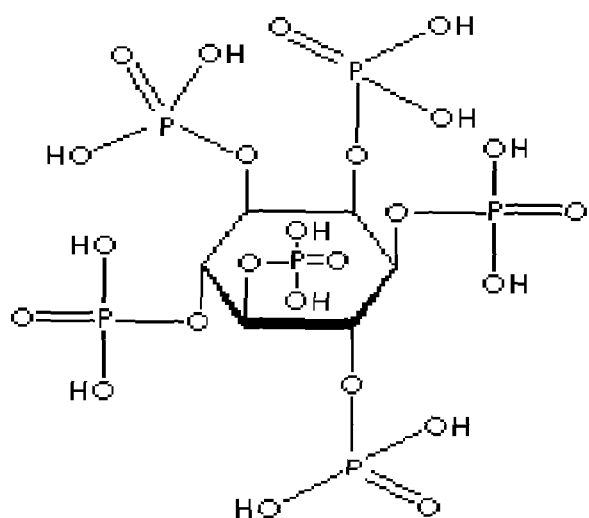
Figure 1. Chemical Structure of Phytic Acid
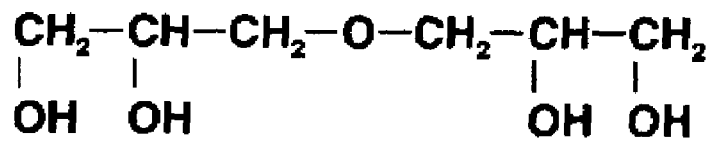
Figure 2. Chemical Structure of Diglycerol
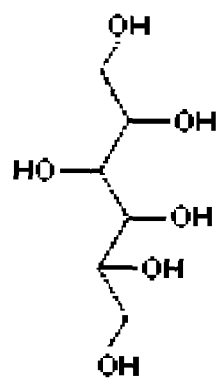
Figure 3. Chemical Structure of Sorbitol.

WATER WASHABLE HAIR REMOVAL (DEPILATORY) COMPOSITIONS

Various compositions and methods for removing hair (depilation) are known. For example, hair can be removed by electrolysis, by chemical action, or by physical removal. Physical removal generally involves the use of wax or tacky tape. Generally, two types of wax for depilatory purposes are used for hair removal, a hot wax or a cold wax. Cold wax is gummy at room temperature, whereas hot wax is hard to medium hard at room temperature. The hot wax compositions are typically heated above their melting point and coated onto the skin. Upon solidification, hair becomes trapped in the wax and is removed when the wax is peeled off the skin. Cold wax compositions do not require such a pre-heating or microwave step prior to their application for depilation. Various depilatory compositions that utilize physical removal action are described in, for example, U.S. Pat. Nos. 6,478,493; 5,847,363; 5,698,187; 5,848,850; 5,846,326; 5,158,765; 5,154,919; 5,840,765; 5,470,563; 4,832,949; 2,091,313 and U.S. Patent application Ser. No. 20030002912 and 20030004522, among others.

One recognized problem with the use of hot waxes and rosin-based compositions is that they require a pre-heating or microwave step prior to their application, and they also inherently incorporate components or impurities that cause irritation that may result in redness, swelling or blisters. Such problems have been discussed in U.S. Patent Application 20010001660 (Romero et al.), and several of the above referenced patents seek to address this problem by utilizing elastomers, or organo-polysiloxane, or by avoiding these ingredients entirely. Romero et al. disclose a hair removal composition that includes beeswax, rosin and an inhibiting salt for inhibiting the irritating agents present primarily as impurities in beeswax and rosin. The composition is heated, applied to the skin and allowed to solidify, embedding hair follicles therein. After solidification, the composition is peeled off the skin. However, any residue left on skin after hair removal cannot be removed by water wash, and solvents are needed for their removal. Many of such solvents are known to cause skin irritation.

As can be appreciated by those versed in the art, the depilatory compositions that require heating or microwave before their application are not convenient. Moreover, they can cause injury or burns, since the heating temperatures cannot be adequately controlled or guessed prior to the application of the heated product on the skin. Furthermore, such compositions are highly sticky that adhere strongly to both hair and skin. During the hair removal step usually the product is applied directly to skin and a fabric or paper is placed over it. After the product has cooled and solidified on the skin, the fabric or paper is pulled away from the skin in a fast motion, thus removing hair. During this process, some epidermal layers of skin are also removed or stripped away, exposing lower layers of skin and initiating inflammatory reaction from prostaglandin formation. Actually, this is the principal reason for the development of skin irritation, and not the minor impurities present in the composition. This fact has not been recognized by prior art. For example, prior art has focused mainly on the use of anti-irritants to circumvent this problem of skin irritation, as disclosed in U.S. Pat. No. 5,470,563 (Tanaka et al.).

In order to solve the problem of damage to skin from such heated depilatory compositions, several "cold-wax" hair removal compositions have been disclosed. Most such compositions are based on sugar or sugar derivatives.

It is commonly recognized that sugar-based compositions do not remove hair adequately in a single application. Sugar and sugar derivatives based compositions also contain substantial amounts of water, or alcohol, or mixtures of water and alcohol, which tend to evaporate each time a bottle is opened for product application, thus resulting in the crystallization of sugar or sugar derivatives from such compositions. Such crystallizations cause a loss of the hair removing power of such compositions, and also make it harder for the bottle to be opened for product use. U.S. Pat. No. 6,417,346 (Salome et al.) further discusses such sugar solution crystallization problems. Additionally, a "dry-down" period is required for such sugar and sugar derivatives based compositions after product applications to let water or alcohol partially evaporate, and before the depilation step is completed. This "dry-down" period can be from 5 minutes to 20 minutes, or even longer. The product does not gain sufficient "stickiness" to remove hair if this "dry-down" period is not observed.

British Letters Patent No. 901,624 (Wenden) discloses the formulation of a cream made up of sugar and lemon juice, glycerin, boric acid powder, sodium chloride and a water carrier. These ingredients are heated, and then allowed to cool to a temperature at which they may be poured into separate jars or containers, and specifically are heated to a temperature on the order of 278 F to form a plastic mass. The resultant composition is applied to the skin so as to become matted with the hair, then immediately stripped from the skin to cause removal of the hair with the plastic mass. However, during their use or storage such compositions still have crystallization problems.

British Letters Pat. No. 1,242,083 (Doughty) also discloses the combination of sugar with citric acid and water in the formation of a depilatory or hair removal composition. Generally, the approach taken in Doughty is to boil the mixture for a short period or optionally to simmer over longer periods but makes no distinction as to the relative effect of boiling versus simmering. Once again the resultant composition is alleged to be of the consistency of paste and which will not harden when applied to the skin and, being water soluble, can be readily cleaned off of the skin; and Doughty proposes the optional addition either of a gelatin or isinglass. It has been found that the use of gelatin tends to leave a burning sensation when applied to the skin as well as to cause swelling and discoloration. Also, during their use or storage such compositions still have crystallization problems.

EP0018668 (Kasidecioglu) disclose a mixture of sugar, water, a weak acid and resin, with the composition 100 parts by weight of sugar, 18 to 20 parts by weight of water, 2 to 6 parts by weight of gum arabic, and 0.2 to 0.4 part by weight of citric acid, tartaric acid or another physiologically acceptable acid suitable for hair removal. However, during their use or storage such compositions still have crystallization problems.

DE10208148 (Hagemann) discloses a depilatory composition comprising of freshly pressed lemon juice 32.25%; melted sugar 64.50%; water 3.25%. The mixture is heated to produce a viscous mass. Since lemon juice is about 91% by weight of water, the actual amount of water in this composition is much higher than 3.25%. Also, during their use or storage such compositions still have crystallization problems.

JP2003040751 (Takako et al.) discloses a depilatory that is comprised of one or more kinds of tackifiers such as a terpene resin, terpene phenol resin, rosin resin, resin acid alcohol, polyvinyl methyl ether, etc., preferably liquid at 70 C, a water-soluble wax such as a polyoxyethylene hardened castor oil, etc., and an emulsifying agent such as a sorbitan fatty acid ester, glycerol fatty acid ester, polyoxyethylene sorbitan fatty acid ester, polyoxyethylene hardened castor oil, etc. Many of such rosin acids are not water-soluble, hence any excess amounts of such compositions left on skin after hair removal are not easily washed by water.

CA2289879 (Brynczka) discloses a cold wax depilatory composition for the removal or hair from the surface of skin. This depilatory composition is comprised of sugar, corn syrup, corn starch, citric acid and water or equivalent ingredients, which produce a pliable, wax-like cold depilatory that adheres to, and efficiently removes hair from the skin surface, without causing any damage or irritation to the skin. However, during their use or storage such compositions still have crystallization problems.

GB2336536 (Guillaume et al.) discloses a depilatory composition that is prepared by heating an aqueous solution of sucrose (60-90% by weight) in the presence of citric or hydrochloric acid and polyethylenimine catalyst until it is substantially free of sucrose. The catalyst allows a shorter time and lower temperature for complete hydrolysis. Excipients, tackifiers and natural waxes or resins are optionally added. The resulting, water-soluble compositions, which do not require reheating before application, are spreadable at room temperature, and can be washed off if misapplied. However, during their use or storage such compositions still have crystallization problems.

GB2336535 (Guillaume et al.) discloses a depilatory composition that is prepared by heating an aqueous solution of sucrose (60-90% by weight) in the presence of citric or hydrochloric acid and optionally a polyethylenimine catalyst until it is substantially free of sucrose and then adding a natural wax or resin. Alternatively the wax or resin is added before the heating process. The resulting, water-soluble compositions, which do not require reheating before application, are spreadable at room temperature, and can be washed off if misapplied. However, during their use or storage such compositions still have crystallization problems.

DE4229392 (Hassoun) discloses a wax-free depilatory composition for mechanical removal of body hair that is made by boiling a mixture. of 580-620 pts.wt. sugar, 80-100 pts.wt. distilled water and 0.7-1.1 ps.wt. citric acid. Boiling is continued for a period such that when cooled to room temperature a brushable paste with a honey-like consistency is obtained. However, during their use or storage such compositions still have crystallization problems.

FR2692144 (Brun) discloses a depilatory composition for application to the body whilst cold to pull out the hairs, comprising a cooked mixture. of sugar and vinegar. However, during their use or storage such compositions still have crystallization problem.

U.S. Pat. No. 5,158,765 (Qasem) discloses a depilatory composition for the removal of hair that is composed of a mixture of sugar, water and aspirin. This mixture is heated to dissolve the solute materials, and then allowed to cool so as to form a soft, pliable composition that can be manually applied to the skin. The composition firmly adheres to the hair with which it comes in contact, and by quickly drawing the applied material away from the skin, will cause the hair to be removed from its roots. One problem from such compositions that are directly applied to skin is that usually an area larger than the area where depilation is needed is coated with such compositions, requiring a more extensive cleanup step after hair removal. Another problem is that such cold-wax compositions based on sugar or sugar derivatives do not remove all the hair in a single step, requiring two or more applications in the same area. This causes waste of product, additional skin irritation, and inconvenience. Also, during their use or storage such compositions still have crystallization problem.

Among other similar sugar-based compositions, U.S. Pat. No. 5,698,187 (Naggiar) discloses depilatory composition for the removal of hair from the human body that is composed of a mixture of maltodextrin, sucrose, water and citric acid. This mixture is heated to dissolve the solute materials, and then cooled to form a soft, pliant composition that can be manually applied to the skin. However, during their use or storage such compositions still have crystallization problem.

U.S. Pat. No. 4,842,610 (Gordon et al.) discloses hair removal compositions that comprise 90 to 99.5% corn syrup and 0.5% to 10% added water by weight. The compositions are used by applying them to the surface of the skin in a hairy area, pressing a sheet of paper or other fibrous material against the area and subsequently lifting the sheet of fibrous material or peeling it off the skin surface. However, during their use or storage such compositions still have crystallization problem.

U.S. Pat. No. 4,832,949 (Royal) discloses a depilatory composition for removal of hair from the human skin that is made up of a mixture of honey, sugar and citric acid which mixture is heated to a predetermined temperature level, then allowed to cool so as to form a highly viscous, wax-like composition which can be applied manually in slender strips to the skin. However, during their use or storage such compositions still have crystallization problem.

Sugar based depilatory compositions are easily washed off from skin after their application, if any residues still remain on the skin after such applications. This single benefit is still one of the most desirable features of sugar-based depilatory compositions. Nad's sugar based depilatory gels, which are currently most popular compositions in consumer market, are reported to contain a mixture of honey, molasses, fructose, vinegar, lemon juice, water, alcohol and food dye. Although these compositions work well for hair removal, they tend to dry-up and develop crystals of unknown composition, as the jars are opened during their use due to the loss of water and alcohol from such compositions. The formation of such crystals then makes such compositions ineffective for hair removal. The same problem is experienced with the commercially available compositions that are based solely on mixtures of sucrose, water, and citric acid. Moreover, the preparation of such sugar and citric acid based compositions requires extended, yet unspecified periods of heating at higher temperatures. For example, U.S. Pat. No. 4,832,949 (Royal) discloses that heating is required for extended periods at temperatures ranging from 245 F to 300 F. This frequently results in compositions that are highly discolored or inconsistent from batch to batch, thus resulting in variable performance for hair removal.

It would thus be advantageous if a depilatory composition can be made that has the following properties: (1) It is applied cold without requiring any pre-heating step, and (2) It is washable with water, and (3) It can be applied either directly on the skin, or, it is first applied on a piece of fabric, plastic, or paper first, which is then applied to skin for hair removal. Alternatively, a dispensing applicator can also be used that can be filled for delivery at the specific site where depilation is desired. Such methods allow the application of product only in the area desired for hair removal, (4) No dry-down period is required, (5) complete depilation is achieved in a single application, (6) Undesirable crystallization is prevented during the use of such compositions, and (7) The preparation of compositions is reasonably uniform from batch to batch under less harsh manufacturing conditions.

The present invention discloses cosmetic cold-wax hair removal (depilatory) compositions suitable for site-specific face or body applications that provide the following benefits:

(1) A pre-heating or microwave step is not necessary, (2) Complete hair removal is achieved in a single application on a specific site or area, (3), No (or minimal) skin irritation is experienced, (4) Can be applied either directly on the skin or, preferably, on a piece of precut fabric, plastic or paper, which is then applied, (5) No dry-down period is required, (6) No undesirable crystallization of ingredients is noted, (7) clean-up of residues left on skin after the application of composition involves simply washing the depilated area with water, (8) The preparation result in consistent compositions from batch to batch, and, as an added benefit, (9) Additional skin and hair beneficial ingredients, such as hair growth retardants, anti-irritants, topical pain relief agents, antioxidants, skin soothing agents, skin cooling agents, emollients, moisturizers, topical anesthetics, colorants, botanical extracts, fragrances, and such can be included in the compositions in addition to usual process-aids such as preservatives and stabilizers.

The present invention discloses cold-wax depilatory compositions that accomplish the above objectives. These compositions are based on: (1) A water-soluble hair binding agent, (2) A water-soluble crosslinking agent for the hair binding agent, and (3) A water-soluble crystallization inhibitor. Optionally, hair growth retardant, skin soothing, anti-irritant, topical analgesic, antioxidant, UV absorber, or other such skin or hair agents or compositions can also be included.

Surprisingly and unexpectedly, it has now been discovered that a combination of a water soluble saccharide as the hair binding agent, a liquid polyhydric alcohol as the crystallization inhibitor, and a polydentate cross-linking agent for the saccharide, for example Phytic acid (FIG. 1), is most suitable as a depilatory composition, provided that, (1) a monosaccharide, or a disaccharide, or a combination is used as the hair binding agent, (2) A water soluble cross-linking agent for the hair binding agent is used to increase the efficacy of the hair binding prowess of the hair binding agent. This is achieved, according to the hypothesis of the present inventor, due to the polyhydroxyl groups of the mono-saccharides or di-saccharides that are cross-linked with the cross-linking agent to form poly-ester derivatives of such saccharides (as evidenced by a reduction in the % weight amount of the saccharide, for example sucrose, by chemical analysis of such compositions, suggestive of a chemical reaction), which forms a mesh of criss-cross molecules of such poly-esterified saccharides on hair, much like weft and warp of a woven fabric. However, this is a hypothesis at this time, and any lack of the knowledge of the actual nature of molecular interconversions that may be occurring via the possible chemical reaction of cross-linking agent with the hair binding agent does not alter the outcome or benefits of the present disclosure, and (3) a water soluble polyhydric alcohol as a crystallization inhibitor, which contains at least six carbon atoms and at least four hydroxylic groups or more, and wherein all hydroxylic groups face the same stereochemical side of the molecule. (For example, diglycerol, which is suitable for the purpose indicated, has the chemical structure as shown in FIG. 2. It contains at least six carbon atoms and four hydroxyls, all facing the same stereochemical side of the molecule. Glycerin, which has only three carbon atoms and three hydroxyl groups, does not perform as well as diglycerol in the compositions of the present invention. Sorbitol, which is unsuitable for the purpose indicated, has six carbon atoms, like diglycerol, and six hydroxyl groups. However, one of the hydroxyl groups of sorbitol faces the opposite side of the stereochemical structure relative to the other five hydroxyl groups, as shown in FIG. (3). For this reason, sorbitol does not perform as well as diglycerol in the compositions of the present invention. The compositions that are made without a cross-linking agent, for example compositions made with a water soluble saccharide as the hair binding agent and a liquid polyhydric alcohol as the crystallization inhibitor, still perform the hair removal function, but the efficacy of such compositions is lesser than the compositions that also include a cross-linking agent. This is because the liquid polyhydric alcohol crystallization inhibitor may also function as a cross-linking agent to some extent, as shall become clearer later. Also, while the cross-linking of thioglycolate-based depilatory compositions is already known, for example U.S. patent application Ser. No. 20020146380 (Nambu et al.), the cross-linking of water soluble saccharide as the hair binding agent is not known in the prior art.

The amount of (1) hair binding agent is from 20 to 90% by weight of the depilatory compositions of the present invention, (2) the polyhydric alcohol is from 2 to 30% by weight of the composition, and (3) the cross-linking agent for the hair binding agent is from 0.1 to 30% by weight of the composition.

The hair-binding agent is selected from water-soluble monosaccharides and disaccharides, and the compositions that contain said saccharides. Monosaccharides and disaccharides are simple sugars of chemical carbohydrate group. Monosaccharide is the simplest sugar. Simple sugars can contain a chain of from four to seven carbon atoms. Such sugars are called tetroses, pentoses, hexoses, and heptoses, respectively. The examples include erythrose, threose, Arabinose, Ribose, Ribulose, Xylose, Xylulose, Lyxose, Allose, Altrose, Fructose, Glucose, Galactose, Gulose, Idose, Mannose, Sorbose, Talose, Tagatose, and Sedoheptulose. Two simple sugars combine to form a disaccharide. The examples of disaccharide include sucrose, lactose, maltose, and trehalose. Of these, only hexoses, and all of disaccharides, are most useful as hair binding agents. Natural or chemical processes can be used to convert monosaccharides into compounds that retain the basic configuration of saccharides, but have different functional groups. Sugar alcohols are, for example, can be made by the hydrogenation of sugars that have an aldehyde or a ketone group. For example, sorbitol is made by the hydrogenation of glucose. Erythrose and Xylose are similarly converted by hydrogenation into erythritol and xylitol, respectively. Although most of these sugar alcohols are useful as hair binding agents, they are more expensive than the monosaccharides of their derivation.

Many saccharide structures differ only in the orientation of the hydroxyl groups. This slight structural difference makes a big difference in the physical, chemical, biological, and organoleptic properties, as shall become clearer later.

The polyhydric alcohol crystallization inhibitor is selected from diglycerol, polyglycerol, triglycerol, tetraglycerol, pentaglycerol, hexaglycerol, and combinations thereof.

The preferred cross-linking agent for the hair binding agent is Phytic acid. Other polyfunctional acids, such as Phosphoric acid, Polyphosphoric acid, Ortho-phosphoric acid, Meta-phosphoric acid, Polysulfonic acid, Alkyl sulfonic acids, Aryl sulfonic acids, Alkyl sulfates (acid form), and Aryl sulfates (acid form) are also suitable for this purpose. The cross-linking agents may be used as their solutions in water, which are more commonly available commercially. For example phytic acid is commonly sold as a 50% solution in water. Similarly, phosphoric acid is sold as water solution in concentration ranging from 50 to 85% by weight. If anhydrous or solid cross-linking agent is used, then water may be added in 5 to 25% by weight to facilitate the mixing and solubilization of water soluble ingredients in such compositions.

Relative to the stereochemical nature of the hydroxyl groups for the polyhydric alcohol crystallization inhibitor agent used in the present invention, it is hypothesized that the facing of the hydroxyl groups on the same side of stereochemistry also provides a better binding with hair due to hydrogen-bond interactions with the hydroxyl groups of the polyhydric alcohol an sulfhydryl groups of the hair, hence a better holding action during the pulling of hair from skin by the hair binding agent. If certain hydroxyl groups are present on the opposite side as well, then they may compete for binding to hair. However, such bonding will be poor, since fewer hydroxyl groups may be present on that side for hydrogen-bond interactions. Diglycerol and Polyglycerol, which are made from glycerol and available from Solvay S.A., Bruxelles, Belgium, among other manufacturers, are most useful as crystallization inhibitors. In a product brochure from Solvay Corporation (www.solvaypolyglycerol.com), it is stated that Diglycerol has the following properties; (i) solubility in water and aqueous systems, (ii) high hydrogen bonding propensity imparting humectant properties to the product, (iii) due to its hydroxyl groups, diglycerol acts as a cross-linking agent for a variety of applications, including the formation of gels, and (iv) environmentally compatible. The cross-linking ability of diglycerol and polyglycerol, hypothetically, may also assist in the increased hair binding ability of the compositions of the present invention. It is also important to mention that both diglycerol and polyglycerol are liquids at 25 C. Other polyhydric alcohols, such as sorbitol, erythritol, and xylitol, are all solids at 25 C. Diglycerol and Polyglycerol thus cannot crystallize from the compositions under conditions of super-saturation, while sorbitol, erythritol, xylitol, and like, can crystallize under the conditions of super-saturation. Moreover, diglycerol and polyglycerol, being liquids at ambient temperatures, provide lubricity during the depilatory applications of the compositions of the present invention. Glycerin is also a polyhydric alcohol, and liquid at 25 C. However, glycerin has only three hydroxyl groups, and for that reason it cannot provide either the hydrogen bonding or the cross-linking ability to the same extent as diglycerol and polyglycerol in the compositions of the present invention.

Additional skin and hair beneficial ingredients or compositions can also be included in the compositions of the present invention. Since a pre-heating or microwave step is not necessary, such additives remain stable and chemically unaltered. The examples include, but not limited to, skin soothing agents, antioxidants, topical anesthetics, antibacterial agents, emollients, moisturizers, skin surface cleansing agents, botanical extracts, perfumes, colorants, preservatives, color stabilizers, antioxidants for rancidity control and such, and combinations thereof can also be included in amounts that are safe and sufficient for their intended benefits and functions.

Although the compositions of the present invention do not cause irritation or pain during depilation process, it may be desirable to include skin cooling and skin numbing agents for some consumers who have delicate, sensitive skin. The examples of such ingredients that can be selected for this purpose includes, but not limited to, menthol, menthol esters, methyl salicylate, camphor, benzocaine, dibucaine, dyclonine, lidocaine, pramoxine, tetracaine, ephedrine, epinephrine, phenylephrine, and their derivatives, and combinations thereof.

The usual ingredients to adjust the pH of the compositions of present invention, for example citric acid, lactic acid, tartaric acid, gluconic acid, Mandelic acid, Salicylic acid, ascorbic acid, gluconolactone, hydrochloric acid, sulfuric acid, phosphoric acid, and such, to better match skin pH can also be included. It should be mentioned here that citric acid and lemon juice have been included as necessary functional ingredients for hair removal in many prior art disclosures for sugar, honey, and corn syrup based depilatory compositions. However, the inclusion of citric acid or lemon juice is not necessary for the hair removal benefits of the composition of the present invention.

The rheology of the compositions of the present invention can be modified, to a certain extent, by a change in the amount of the hair binding agent in such compositions. The compositions of the present invention can additionally include one or more alternate rheological modifiers. The rheological modifiers that can be used in this invention include, but are not limited to high molecular weight crosslinked homopolymers of acrylic acid, and Acrylates/C10-30 Alkyl Acrylate Crosspolymer, such as the Carbopol. and Pemulen series, both available from B. F. Goodrich, Akron, Ohio, USA; anionic acrylate polymers such as Salcare and cationic acrylate polymers such as Salcare SC96, available from Ciba Specialties, High Point, N.C., USA; Acrylamidopropyltrimonium chloride/acrylamide; Hydroxyethyl methacrylates polymers, Steareth-10 Allyl Ether/Acrylate Copolymer; Acrylates/Beheneth-25 Methacrylate Copolymer, known as Aculyn, available from International Specialties, Wayne, N.J., USA; Glyceryl Polymethacrylate, Acrylates/Steareth-20 Methacrylate Copolymer; bentonite; gums such as alginates, carageenan, gum acacia, gum arabic, gum ghatti, gum karaya, gum tragacanth, guar gum; guar hydroxypropyltrimonium chloride, xanthan gum, gellan gum; cellulose derivatives such as sodium carboxymethyl cellulose, hydroxyethyl cellulose, hydroxymethyl carboxyethyl cellulose, hydroxymethyl carboxypropyl cellulose, ethyl cellulose, sulfated cellulose, hydroxypropyl cellulose, methyl cellulose, hydroxypropylmethyl cellulose, microcrystalline cellulose; agar; pectin; gelatin; starch and its derivatives; chitosan and its derivatives such as hydroxyethyl chitosan; polyvinyl alcohol (PVA), PVM/MA copolymer, PVM/MA decadiene crosspolymer, poly (ethylene oxide) based thickeners, sodium carbomer, and mixtures thereof. When used, the rheology modifiers are preferably included in the cosmetically acceptable composition of this invention at a concentration of from 0.01 to 12 weight percent, preferably from 0.05 to 10 weight percent, and most preferably from 0.1 to 2 weight percent.

The preparation of only non-microwave compositions is not a limitation of the present invention. The microwave versions, if so desired, can be prepared by an adjustment of the rheology (viscosity) of such compositions. This can be achieved, as one can expect, by increasing the amount of monosaccharide or disaccharide or the use of a rheology modifier in such compositions. Example 12 provides an illustration of such a composition.

Also, other cosmetically appealing forms of water washable depilatory compositions can be made by the present disclosure. Depilatory clay, for example, can be made by the inclusion of from 0.1 to 10% by weight, or even more, of suitable clay, such as bentonite, montmorillonite, zeolite, alumina, silicates, and such.

or more. The cosmetically acceptable composition of this invention may include one or more preservatives. Example of preservatives, which may be used include, but are not limited to 1,2-dibromo-2,4-dicyano butane (Methyidibromo Glutaronitrile, known as MERGUARD. Nalco Chemical Company, Naperville, Ill., USA), benzyl alcohol, imidazolidinyl urea, 1,3-bis(hydroxymethyl)-5,5-dimethyl-2,3-imidazolidinedione (e.g., DMDM Hydantoin, known as GLYDANT, Lonza, Fairlawn, N.J., USA.), methylchloroisothiazolinone and methylisothiazolinone (e.g., Kathon, Rohm & Haas Co., Philadelphia, Pa., USA), methyl paraben, propyl paraben, phenoxyethanol, and sodium benzoate, phenoxyethanol, ethylhexylglycerin, Chlorphenesin, dehydroacetic acid, and mixtures thereof.

EXAMPLES

The following examples are presented to illustrate presently preferred practice thereof. As illustrations they are not intended to limit the scope of the invention. All quantities are in weight %. Some of the Examples are duplication of prior art disclosures, the purpose of which is to compare such compositions for their depilatory property with the compositions of the present invention by a consumer panel.

Example 1

Ingredients. (1) Diglycerol 10.0 (2) Water 19.0 (3) Sucrose 70.0 (4) Preservative 1.0. Procedure. Mix (2) to (4) and heat at 90 to 95 C for 30 to 45 minutes to a clear liquid. Add (1) and mix. Cool to room temperature. A clear, light amber mobile liquid is obtained. It is applied to skin or pre-cut fabric, plastic, or paper without any pre-heating or microwave.

Example 2

Ingredients. (1) Diglycerol 10.0 (2) Water 15.0 (3) Sucrose 72.0 (4) Preservative 1.0 (5) Citric acid 2.0. Procedure. Mix (2) to (5) and heat at 90 to 95 C for 30 to 45 minutes to a clear liquid. Add (1) and mix. Cool to room temperature. A clear, light amber mobile liquid is obtained. It is applied to skin or pre-cut fabric, plastic, or paper without any pre-heating or microwave.

Example 3

Ingredients. (1) Diglycerol 10.0 (2) Sucrose 77.0 (3) Phytic acid (10% solution in water) 12.0 (4) Preservative 1.0. Procedure. Mix (2) to (4) and heat at 90 to 95 C for 30 to 45 minutes to a clear liquid. Add (1) and mix. Cool to room temperature. A clear, light amber mobile liquid is obtained. It is applied to skin or pre-cut fabric, plastic, or paper without any pre-heating or microwave.

Example 4

Ingredients. (1) Glycerin 10.0 (2) Water 12.0 (3) Sucrose 75.0 (4) Preservative 1.0 (5) Citric acid 2.0. Procedure. Mix (2) to (5) and heat at 90 to 95 C for 30 to 45 minutes to a clear liquid. Add (1) and mix. Cool to room temperature. A clear, light amber mobile liquid is obtained. It is applied to skin or pre-cut fabric, plastic, or paper without any pre-heating or microwave.

Example 5

Ingredients. (1) Diglycerol 10.0 (2) Water 12.0 (3) Sucrose 75.0 (4) Preservative 1.0 (5) Citric acid 2.0. Procedure. Mix (2) to (5) and heat at 90 to 95 C for 30 to 45 minutes to a clear liquid. Add (1) and mix. Cool to room temperature. A clear, light amber mobile liquid is obtained. It is applied to skin or pre-cut fabric, plastic, or paper without any pre-heating or microwave.

Example 6

Ingredients. (1) Sorbitol 10.0 (2) Sucrose 75.0 (3) Preservative 1.0 (4) Phytic acid 1.0 (5) Citric acid 1.0 (6) Water 12.0.
Procedure. Mix all components and heat at 90 to 95 C for 30 to 45 minutes to a clear liquid. Cool to room temperature. A clear, light amber mobile liquid is obtained. It is applied to skin or pre-cut fabric, plastic, or paper without any pre-heating or microwave.

Example 7

Consumer Testing of Compositions of Example 1 to Example 6. A six person panel, all female, tested the compositions of example 1 to example 5 by direct application on skin and also the application of the product first on fabric pieces, then the application of such coated fabric pieces on skin for depilation. No dry-down period was observed. Procedure: (1) Hair should be at least ¼" long for the test. (2) Squeeze test composition, out of tube, directly onto non-woven depilatory strip. (3) With an appropriate applicator, spread test composition in an even, thin, layer onto strip. (4) Place pre-coated strip onto desired treatment area of skin. (5) Gently rub the top of strip in the direction of hair growth. (6) Once strip seems secure (5 to 10 seconds), hold skin taut, and with the other hand grasp the edge of the coated depilatory strip. (7) With a quick, but nice and even motion, remove wax strip, pulling in the opposite direction of hair growth.

The ratings, based on ease of product application, completeness of hair removal in a single treatment, ease of cleanup after use, and amount of skin irritation, from most preferred to least preferred, follow: Example 3=Example 5>Example 2>Example 1>Example 6>Example 4.

Two commercially purchased products, a sugar based "cold-wax" product, and the same group of panelists, then tested rosin based "microwave" product, and composition of Example 3. The ratings, based on ease of product application, completeness of hair removal in a single treatment, ease of cleanup after use, and amount of skin irritation, from most preferred to least preferred, follow: Example 3>>Commercial Sucrose-based product>Commercial Rosin based product.

Example 8

Ingredients. (1) Diglycerol 10.0 (2) Sucrose 75.0 (3) Phosphoric acid (1.8% solution in water) 14.0 (4) Preservative 1.0. Procedure. Mix (2) to (4) and heat at 90 to 95 C for 30 to 45 minutes to a clear liquid. Add (1) and mix. Cool to room temperature. A clear, light amber mobile liquid is obtained. It is applied to skin or pre-cut fabric, plastic, or paper without any pre-heating or microwave.

Example 9

Ingredients. (1) Polyglycerol 10.0 (2) Sucrose 75.0 (3) Phosphoric acid (1.8% solution in water) 14.0 (4) Preservative 1.0. Procedure. Mix (2) to (4) and heat at 90 to 95 C for 30 to 45 minutes to a clear liquid. Add (1) and mix. Cool to room temperature. A clear, light amber mobile liquid is obtained. It is applied to skin or pre-cut fabric, plastic, or paper without any pre-heating or microwave.

Example 10

Consumer Testing of Compositions of Example 3, Example 8 and Example 9. A six person panel, all female, tested the compositions of Examples 3, 8, and 9 of the present invention by their direct application on skin and also the application of the product first on fabric pieces, then the application of such coated fabric pieces on skin for depilation.

No dry-down period was observed. Procedure: (1) Hair should be at least ¼" long for the test. (2) Squeeze test composition, out of tube, directly onto non-woven depilatory strip. (3) With an appropriate applicator, spread test composition in an even, thin, layer onto strip. (4) Place pre-coated strip onto desired treatment area of skin. (5) Gently rub the top of strip in the direction of hair growth. (6) Once strip seems secure (5 to 10 seconds), hold skin taut, and with the other hand grasp the edge of the coated depilatory strip. (7) With a quick, but nice and even motion, remove wax strip, pulling in the opposite direction of hair growth.

The ratings, based on ease of product application, completeness of hair removal in a single treatment, ease of cleanup after use, and amount of skin irritation, from most preferred to least preferred, follow: Example 3>Example 8=Example 9.

Example 11

Stability Testing of Compositions of Example 3, Example 8 and Example 9. The samples of these compositions were placed in open glass jars (no lids), which were placed in an oven at 50 C for one week. No crystallization was noted. However, the compositions did become more viscous and turned brown, possibly due to such extended period of exposure to heat. Their hair removal efficacy was intact.

Example 12

Microwave Water Washable Depilatory Composition. Ingredients. (1) Diglycerol 10.0 (2) Sucrose 79.0 (3) Phytic acid (10% solution in water) 10.0 (4) Preservative 1.0. Procedure. Mix (2) to (4) and heat at 90 to 95 C for 30 to 45 minutes to a clear liquid. Add (1) and mix. Cool to room temperature. A clear, thick paste is obtained. It is applied to skin or pre-cut fabric, plastic, or paper after pre-heating or microwave to make it softer.

Example 13

Microwave Water Washable Depilatory Composition. Ingredients. (1) Diglycerol 10.0 (2) Sucrose 78.2 (3) Phytic acid (10% solution in water) 10.0 (4) Polyvinyl alcohol 0.2 (5) Preservative 1.0. Procedure. Mix (2) to (5) and heat at 90 to 95 C for 30 to 45 minutes to a clear liquid. Add (1) and mix. Cool to room temperature. A clear, light amber thick paste is obtained. It is applied to skin or pre-cut fabric, plastic, or paper after pre-heating or microwave to make it softer.

Example 14

Water Washable Depilatory Composition with Emolliency. Ingredients. (1) Diglycerol 30.0 (2) Sucrose 58.0 (3) Phytic acid (10% solution in water) 10.0 (4) Amodimethicone (and) Trideceth-12 (and) Cetrimonium Chloride 1.0 (5) Preservative 1.0. Procedure. Mix (2) and (3) and heat at 90 to 95 C for 30 to 45 minutes to a clear liquid. Add (1), ((4) and (5) and mix. Cool to room temperature. A clear, mobile liquid is obtained. It is applied to skin or pre-cut fabric, plastic, or paper without any pre-heating or microwave.

Example 15

Water Washable Depilatory Clay Composition. Ingredients. (1) Diglycerol 10.0 (2) Sucrose 75.0 (3) Phytic acid (10% solution in water) 10.0 (4) Preservative 1.0 (5) White Clay 4.0. Procedure. Mix (2) to (4) and heat at 90 to 95 C for 30 to 45 minutes to a clear liquid. Add (1) and (5) and mix. Cool to room temperature. An opaque mobile liquid is obtained. It is applied to skin or pre-cut fabric, plastic, or paper without any pre-heating or microwave.

Example 16

Depilatory and Skin Refining Facial Clay Composition. Ingredients. (1) Diglycerol 10.0 (2) Sucrose 74.9 (3) Phytic acid (10% solution in water) 10.0 (4) Preservative 1.0 (5) Polyvinyl alcohol 0.1 (6) Zeolite 4.0. Procedure. Mix (2) to (5) and heat at 90 to 95 C for 30 to 45 minutes to a clear liquid. Add (1) and (6) and mix. Cool to room temperature. An opaque mobile liquid is obtained. It is applied to skin or pre-cut fabric, plastic, or paper without any pre-heating or microwave.

BRIEF DESCRIPTION OF DRAWINGS

FIG. 1. Chemical Structure of Phytic Acid.
FIG. 2. Chemical Structure of Diglycerol.
FIG. 3. Chemical Structure of Sorbitol.

What is claimed is:

1. A cosmetic cold-wax depilatory composition produced by a process comprising: (1) mixing a water soluble hair binding agent, a water soluble cross-linking agent for the hair binding agent, and a water soluble crystallization inhibitor, (2) heating the mixture to a temperature of 80 to 95 degrees Celsius for 30 to 45 minutes, and (3) allowing the resulting product to cool to room temperature wherein the water soluble hair binding agent is selected from the group consisting of sucrose, glucose, fructose, lactose, corn syrup, honey, molasses, and combinations thereof, and wherein the water soluble crystallization inhibitor is a liquid at 25 degrees Celsius, and wherein the water soluble crystallization inhibitor comprises a polyhydroxy alcohol selected from the group consisting of diglycerol, triglycerol, tetraglycerol, pentaglycerol, hexaglycerol, polyglycerol and combinations thereof, and wherein the water soluble crystallization inhibitor has at leas six carbon atoms and at least four hydroxyl groups, said at least four hydroxyl groups being on the same side of the stereochemical configuration of said water soluble crystallization inhibitor, and wherein said cross-linking agent for the hair binding agent is phytic acid.

2. The composition of claim 1, wherein the hair binding agent is sucrose.

3. The composition of claim 1, wherein the hair binding agent is from 10% to 90% by weight of the composition.

4. The composition of claim 1, wherein the water soluble crystallization inhibitor is diglycerol.

5. The composition of claim 1, wherein the water soluble crystallization inhibitor is polyglycerol.

6. The composition of claim 1, wherein the water soluble crystallization inhibitor is from 2% to 80% by weight of the composition.

7. The composition of claim 1, wherein the water soluble cross-linking agent is from 0.01% to 20% by weight of the composition.

8. The composition of claim 1 further comprising water, wherein the water content is up to 25% by weight of the composition.

9. The composition of claim 1 further comprising clay.

10. The composition of claim 1 further comprising preservatives, colorants, pigments, color stabilizers, emollients, moisturizers, skin surface cleansing agents, antibacterial agents, anti-wrinkle agents, anti-aging additives, botanical extracts, skin soothing agents, topical pain relief agents, skin smoothing agents, UV absorbers, fragrances, antioxidants, chelating agents and combinations thereof.

11. The composition of claim 1, wherein the composition is contained in dispensing applicators selected from the group consisting of roll-on, glide-on, push-up, heated containers, jars and tubes.

12. The composition of claim 1, wherein the composition is a coating on a surface selected from the group consisting of fabric, paper, plastic and combinations thereof.

13. The composition of claim 1, wherein the composition is contained in dispensing applicators selected from the group consisting of roll-on, glide-on, push-up, heated containers, jars and tubes.

14. The composition of claim 1, wherein (i) the hair binding agent is sucrose, present from about 10% to 85% by weight of the composition, and wherein (ii) the water soluble crystallization inhibitor is present from about 2% to 80% by weight of the composition and is selected from the group consisting of diglycerol, polyglycerol or a combination thereof, and wherein (iii) the water soluble cross-linking agent is phytic acid, present from about 0.1% to 10% by weight of the composition, and (iv) further comprising water, present from about 2% to 30% by weight of the composition.

15. A method of removing hair from human skin comprising applying a composition of claim 1 to human skin, allowing the composition to adhere to hair, and removing the composition and hair from human skin.

16. The method of claim 15, wherein the composition is applied in strips selected from fabric strips, paper strips, plastic strips, or combinations thereof.

17. A method of removing hair from human skin comprising applying a composition of claim 14 to human skin, allowing the composition to adhere to hair, and removing the composition and hair from human skin.

* * * * *